United States Patent [19]

Nakamura et al.

[11] Patent Number: 5,031,628
[45] Date of Patent: Jul. 16, 1991

[54] ULTRASONIC BLOOD VELOCITY DETECTOR

[75] Inventors: Yasuhiro Nakamura, Tokyo; Ikuo Sakai, Kawasaki; Masami Kawabuchi, Yokohama, all of Japan

[73] Assignee: Matsushita Electric Industrial Co., Ltd., Japan

[21] Appl. No.: 364,727

[22] Filed: Jun. 12, 1989

[30] Foreign Application Priority Data

Jun. 15, 1988 [JP] Japan .................................. 63-147460

[51] Int. Cl.$^5$ .............................................. A61B 8/00
[52] U.S. Cl. ............................. 128/661.09; 73/861.25
[58] Field of Search ...................... 128/661.09, 661.10; 73/861.25

[56] References Cited

U.S. PATENT DOCUMENTS 4,554,926 11/1985 Shirasaka ...................... 128/661.09
4,896,674 1/1990 Seo ................................ 128/661.09

FOREIGN PATENT DOCUMENTS 0081045  6/1983 European Pat. Off. ....... 128/661.09
0166392  1/1986 European Pat. Off. ....... 128/661.09
0202920 11/1986 European Pat. Off. ....... 128/661.09
0217953  4/1987 European Pat. Off. ....... 128/661.09

OTHER PUBLICATIONS

Fehr, R. et al., "A New MTI Structure with Inherent Analog -to-Digital Conversion", Conf. Ckt Theory and Design, Lausanne, Switzerland (4-8 Sep. 1978).

Primary Examiner—Francis Jaworski
Attorney, Agent, or Firm—Lowe, Price, LeBlanc, Becker & Shur

[57] ABSTRACT

An ultrasonic blood velocity detector comprises an ultrasonic probe emitting ultrasonic wave into an examined body and converting echoes of the emitted ultrasonic wave into an echo signal. The echo signal is processed into a detection signal through phase detection. A first Doppler signal and a second Doppler signal are derived from the detection signal. The first Doppler signal represents a flow of blood. The second Doppler signal mainly contains clutter components. A difference in phase between the first and second Doppler signals is calculated.

3 Claims, 4 Drawing Sheets

ULTRASONIC BLOOD VELOCITY DETECTOR

BACKGROUND OF THE INVENTION

1. Field of the Invention

This invention relates to an ultrasonic blood velocity detector using the Doppler shifts.

2. Description of the Prior Art

Blood velocity can be detected by measuring the Doppler shifts in frequency imparted to ultrasound by reflection from moving red blood cells. There are various ultrasonic blood velocity detectors using such a Doppler method.

"New ultrasonic diagnostic technique", Clinical Ultrasonic Wave Series 9, published in 1984, page 86, discloses one example of such an ultrasonic Doppler blood velocity detector. This prior art detector uses high pass filters in separating blood velocity Doppler signals and clutter signals caused by motions of internal organs within an examined body. It should be noted that the clutter signals decrease the accuracy of the measurement of the blood velocity. In the prior art detector, when a low blood velocity is measured, the clutter signals are close to the blood velocity Doppler signals in frequency so that the high pass filters tend to inadequately separate the blood velocity Doppler signals and the clutter signals. The inadequate separation results in a decreased accuracy of the measurement of the blood velocity.

SUMMARY OF THE INVENTION

It is an object of this invention to provide an accurate ultrasonic blood velocity detector.

An ultrasonic blood velocity detector of this invention comprises an ultrasonic probe emitting ultrasonic wave into an examined body and converting echoes of the emitted ultrasonic wave into an echo signal. The echo signal is processed into a detection signal through phase detection. A first Doppler signal and a second Doppler signal are derived from the detection signal. The first Doppler signal represents a flow of blood. The second Doppler signal mainly contains clutter components. A difference in phase between the first and second Doppler signals is calculated.

DESCRIPTION OF THE FIRST PREFERRED EMBODIMENT

Figure 1:
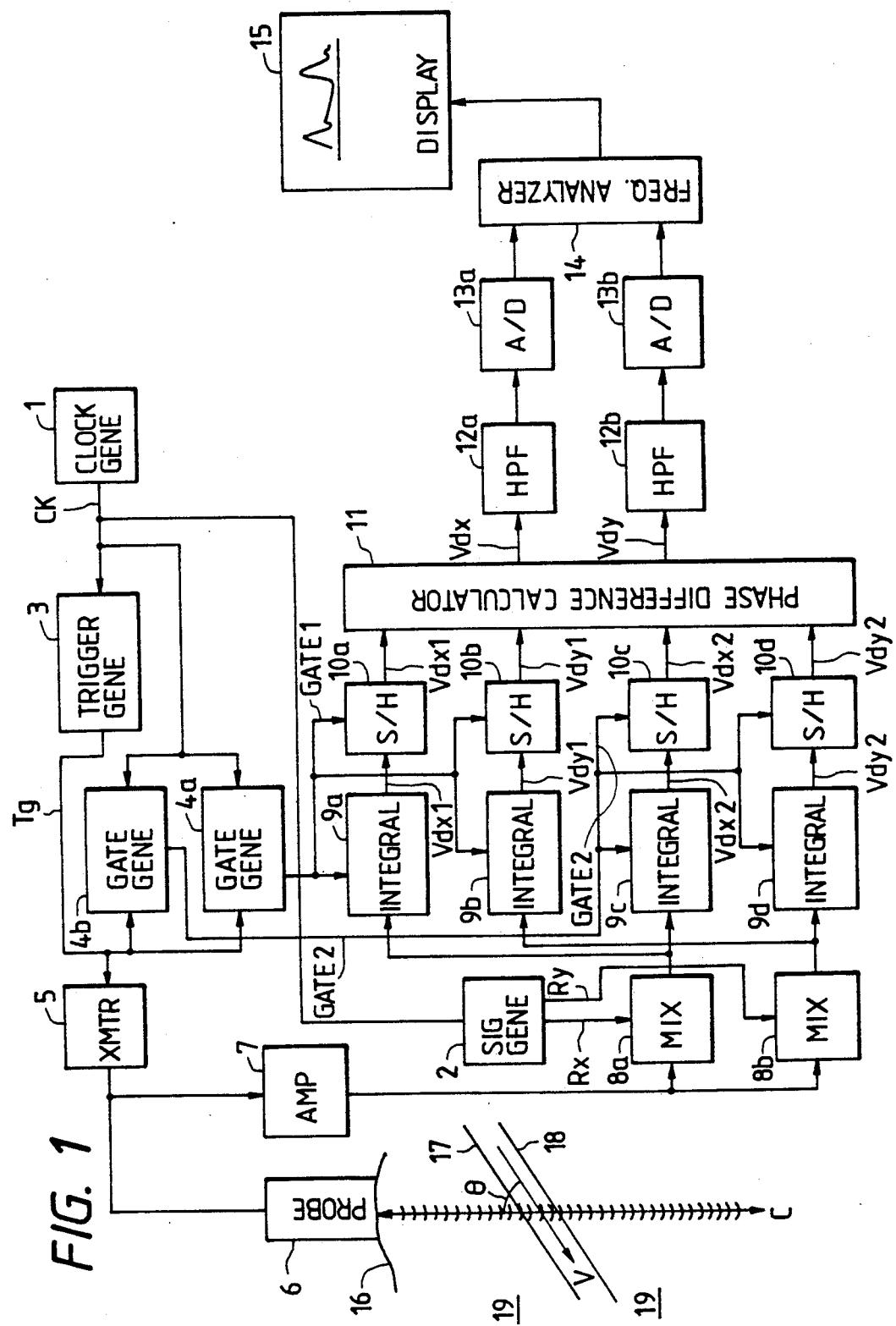
FIG. 1 is a block diagram of an ultrasonic blood velocity detector according to a first embodiment of this invention.

With reference to FIG. 1, a pulse-type ultrasonic blood velocity detector includes a clock generator 1 which outputs a clock signal CK to an orthogonal (quadrature) signal generator 2, a trigger signal generator 3, and gate signal generators 4a and 4b.

The orthogonal signal generator 2 derives a pair of orthogonal or quadrature reference signals Rx and Ry from the clock signal CK through a frequency division process and a phase shift process. The reference signals Rx and Ry are orthogonal to each other and have a phase difference of 90°. The trigger signal generator 3 derives a trigger pulse signal Tg from the clock signal CK through a frequency division process. The trigger signal Tg is fed to the gate signal generators 4a and 4b. The gate signal generator 4a counts pulses of the clock signal CK and outputs a gate signal GATE1 at a predetermined time measured from a reference timing determined by the trigger signal Tg. Similarly, the gate signal generator 4b outputs a gate signal GATE2 at a predetermined time measured from the reference timing.

The trigger signal Tg is also fed to a transmitter 5. The transmitter 5 generates a drive pulse signal synchronous with the trigger signal Tg. The drive pulse signal is outputted from the transmitter 5 to an ultrasonic probe 6. The ultrasonic probe 6 converts the drive pulse signal into pulses of beam of corresponding ultrasonic wave and emits the ultrasonic beam pulses into an examined body 16. Echoes of the ultrasonic beam pulses are generated within the body 16 and portions of the echoes return to the ultrasonic probe 6. The ultrasonic probe 6 converts the ultrasonic echoes into a corresponding echo signal or received signal.

The echo signal is fed from the ultrasonic probe 6 to mixers 8a and 8b via an amplifier 7. The mixer 8a processes the received signal into a first detection signal through orthogonal detection or phase detection by use of the reference signal Rx outputted from the orthongonal signal generator 2. Similarly, the mixer 8b processes the received signal into a second detection signal through orthogonal detection or phase detection by use of the reference signal Ry outputted from the orthogonal signal generator 2.

An integrator 9a integrates the first detection signal during a period determined by the gate signal GATE1. An integrator 9b integrates the second detection signal during the period determined by the gate signal GATE1. The integrators 9a and 9b output a pair of first orthogonal Doppler signals Vdx1 and Vdy1 respectively.

An integrator 9c integrates the first detection signal during a period determined by the gate signal GATE2. An integrator 9d integrates the second detection signal during the period determined by the gate signal GATE2. The integrators 9c and 9d output a pair of second orthogonal Doppler signals Vdx2 and Vdy2 respectively.

Sample-and-hold circuits 10a and 10d sample the first Doppler signals Vdx1 and Vdy1 respectively at a timing determined by the gate signal GATE1 and hold the sampled signals Vdx1 and Vdy1 until the subsequent sampling. Sample-and-hold circuits 10c and 10d sample the second Doppler signals Vdx2 and Vdy2 respectively at a timing determined by the gate signal GATE2 and hold the sampled signals Vdx2 and Vdy2 until the subsequent sampling.

A phase difference calculator 11 determines a phase difference between the first Doppler signals Vdx1 and Vdy1 and the second Doppler signals Vdx2 and Vdy2 outputted from the sample-and-hold circuits 10a–10d. The phase difference calculator 11 derives a pair of orthogonal final Doppler signals Vdx and Vdy from the first and second Doppler signals through the phase difference calculation.

The final Doppler signals Vdx and Vdy are fed from the phase difference calculator 11 to analog-to-digital converters 13a and 13b via high pass filters 12a and 12b respectively. The high pass filters 12a and 12b remove clutter components from the Doppler signals Vdx and Vdy. The devices 13a and 13b convert the Doppler signals Vdx and Vdy into corresponding digital Doppler signals applied to a frequency analyzer 14. The device 14 analyzes the frequency of the digital Doppler signals. A display 15 indicates a result of the frequency analysis of the digital Doppler signals which is performed by the frequency analyzer 14.

Figure 2:
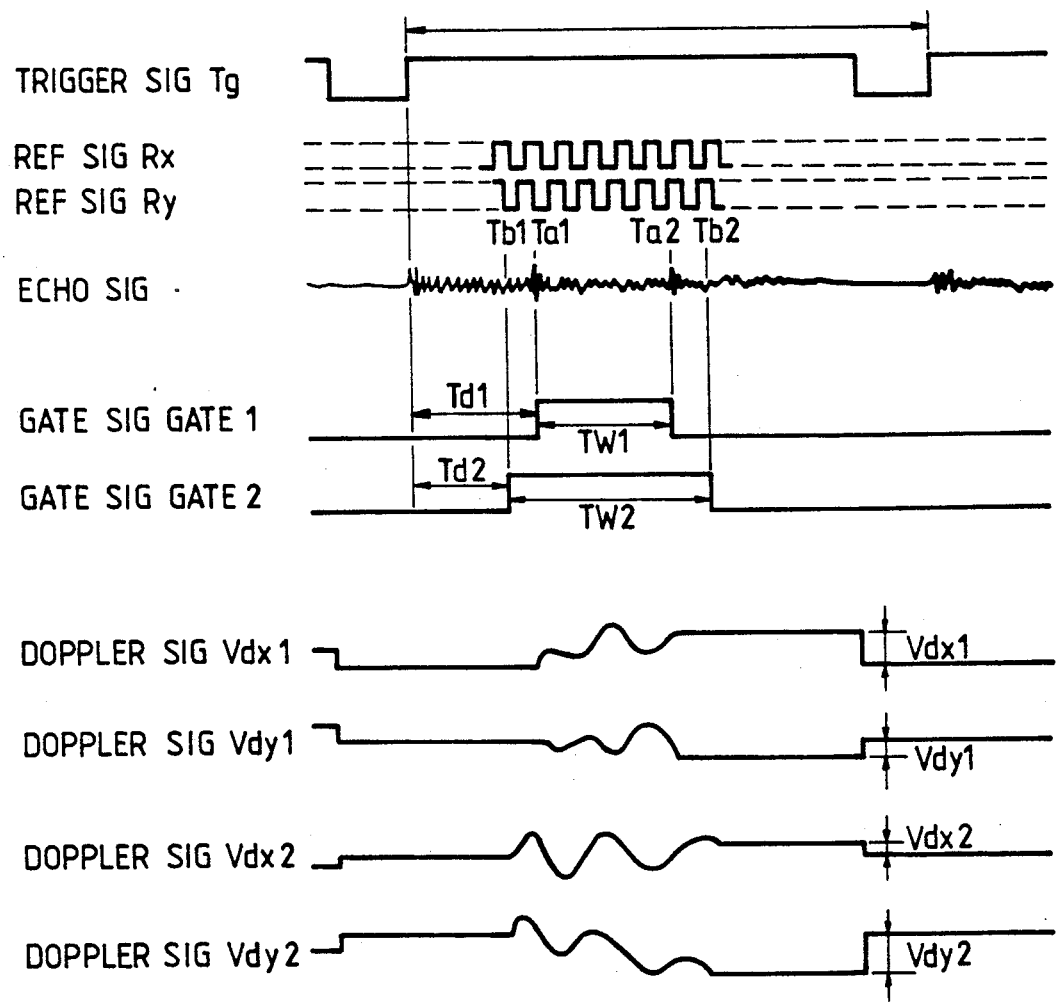
FIG. 2 is a timing chart showing the waveforms of various signals in the ultrasonic blood velocity detector of FIG. 1.

The ultrasonic blood velocity detector operates as follows. The clock generator 1 outputs the clock signal CK. The orthogonal signal generator 2 derives a pair of the orthogonal reference signals Rx and Ry from the clock signal CK through a frequency division process and a phase shift process. As shown in FIG. 2, the reference signals Rx and Ry are 90° out of phase from each other. The trigger signal generator 3 derives the trigger pulse signal Tg from the clock signal CK through a frequency division process. As shown in FIG. 2, the trigger signal Tg has a constant period.

The gate signal generator 4a starts to count pulses of the clock signal CK in response to the trigger signal Tg and outputs the gate signal GATE1 including a pulse synchronous with the trigger signal Tg. As shown in FIG. 2, the gate signal pulse GATE1 starts at a moment Ta1 which follows the trigger pulse Tg by a predetermined delay time Td1. The gate signal pulse GATE1 lasts for a predetermined interval Tw1 and terminates at a moment Ta2. Similarly, the gate signal generator 4b starts to count pulses of the clock signal CK in response to the trigger signal Tg and outputs the gate signal GATE2 including a pulse synchronous with the trigger pulse Tg. As shown in FIG. 2, the gate signal pulse GATE2 starts at a moment Tb1 which follows the trigger pulse Tg by a predetermined delay time Td2. The moment Tb1 of the start of the gate signal pulse GATE2 is close to the moment Ta1 of the start of the gate signal pulse GATE1. The gate signal pulse GATE2 lasts for a predetermined interval Tw2 and terminates at a moment Tb2. The moment Tb2 of the termination of the gate signal pulse GATE2 is close to the moment Ta2 of the termination of the gate signal pulse GATE1.

The transmitter 5 generates the drive pulse signal in response to the trigger signal Tg. The drive pulse signal is outputted to the ultrasonic probe 6 in contact with the examined body 16. The ultrasonic probe 6 converts the drive pulse signal into pulses of a beam of corresponding ultrasonic wave and emits the ultrasonic beam pulses into the examined body 16. Echoes of the ultrasonic beam pulses are generated at internal portions of the examined body 16 such as organs 19, a blood vessel 17, and blood 18 within the blood vessel 17. Parts of the echoes return to the ultrasonic probe 6. The ultrasonic probe 6 converts the ultrasonic echoes into the corresponding echo signal or received signal.

One example of the waveform of the echo signal is shown in FIG. 2. The echo signal includes echo components which occur at respective moments dependent upon the distances from the surface of the examined body 16 to the positions of the generation of the corresponding ultrasonic echoes. In one example, the echo components which result from the ultrasonic echoes generated at the front walls and the rear walls of the blood vessel 17 are present at the moments Ta1 and Ta2 respectively while the echo components which result from the ultrasonic echoes generated by the blood 18 are present for the interval between the moments Ta1 and Ta2. In addition, the echo components which result from the ultrasonic echoes generated at the other portions of the examined body 16 are present during a period except the interval between the moments Ta1 and Ta2.

It is preferable that the duration Tw1 of the gate signal pulse GATE1 is equal to or shorter than the duration Tw2 of the gate signal pulse GATE2. The gate signal pulse GATE1 is designed to last for the period during which the echo signal mainly corresponds to the ultrasonic echoes generated by the blood 18. The gate signal pulse GATE2 is designed to last for the period during which the echo signal corresponds to the ultrasonic echoes generated by the blood 18, the blood vessel 17, and also the organs 19 surrounding the blood vessel 17.

The echo signal or received signal is fed from the ultrasonic probe 6 to the mixers 8a and 8b via the amplifier 7. The mixer 8a mixes the echo signal and the reference signal Rx and specifically processes the echo signal into the first detection signal through orthogonal detection or phase detection by use of the reference signal Rx. Similarly, the mixer 8b mixes the echo signal and the reference signal Ry and specifically processes the echo signal into the second detection signal through orthogonal detection or phase detection by use of the reference signal Ry.

The integrator 9a integrates the first detection signal during the interval corresponding to the duration Tw1 of the gate signal pulse GATE1. The integrator 9b integrates the second detection signal during the interval corresponding to the duration Tw1 of the gate signal pulse GATE1. The integrators 9a and 9b output a pair of the first orthogonal Doppler signals Vdx1 and Vdy1 which represent the flow of the blood 18. One example of the waveforms of the first Doppler signals Vdx1 and Vdy1 is shown in FIG. 2.

The integrator 9c integrates the first detection signal during the interval corresponding to the duration Tw2 of the gate signal pulse GATE2. The integrator 9d integrates the second detection signal during the interval corresponding to the duration Tw2 of the gate signal pulse GATE2. The integrators 9c and 9d output a pair of the second orthogonal Doppler signals Vdx2 and Vdy2 which represent the flow of the blood 18 and also the motion of the organs 19 surrounding the blood vessel 17. One example of the waveforms of the second Doppler signals Vdx2 and Vdy2 is shown in FIG. 2.

The sample-and-hold circuits 10a and 10b sample the first Doppler signals Vdx1 and Vdy1 at the moment Ta2 determined by the gate signal GATE1 and hold the sampled signals Vdx1 and Vdy1 until the subsequent sampling moment. The sample-and-hold circuits 10c and 10d sample the second Doppler signals Vdx2 and Vdy2 at the moment Tb2 determined by the gate signal GATE2 and hold the sampled signals Vdx2 and Vdy2 until the subsequent sampling moment.

In the first Doppler signals Vdx1 and Vdy1 held by the sample-and-hold circuits 10a and 10b, Doppler components which result from the flow of the blood 18 are modulated by clutter components corresponding to Doppler components caused by the motion of the organs 19. The Doppler shift frequency fdo is expressed by the following equation (1).

$$fdo = \{2 \cdot (V1 + V2)/C\} \cdot fc \cdot \cos\theta \qquad (1)$$

where the character V1 denotes the velocity of the blood 18; the character V2 denotes the velocity of the organs 19; the character C denotes the speed of sound in the ultrasonic propagation medium; the character fc denotes the frequency of the ultrasonic wave; and the character $\theta$ denotes the angle between the direction of the travel of the ultrasonic wave and the direction of the flow of the blood 18.

The Doppler shift frequency fdo is decomposed into an accurate signal part fd1 and a clutter part fd2 as expressed in the following equation (2).

$$fdo = fd1 + fd2 \quad (2)$$

where the component fd1 results from the flow of the blood 18 and the component fd2 results from the motion of the organs 19. Accordingly, the first Dopper signals Vdx1 and Vdy1 are expressed by the following equations (3) and (4) including the accurate signal component fd1 and the clutter component fd2.

$$Vdx1 = A1 \cdot \cos\{2\pi \cdot (fd1 + fd2) \cdot t\} \quad (3)$$

$$Vdy1 = A1 \cdot \sin\{2\pi \cdot (fd1 + fd2) \cdot t\} \quad (4)$$

where the character A1 denotes a constant representing the amplitude.

The second Doppler signals Vdx2 and Vdy2 held by the sample-and-hold circuits 10c and 10d mainly include clutter components caused by the motion of the organs 19. The Doppler shift frequency fd2 related to the motion of the organs 19 is expressed by the following equation (5).

$$fd2 = (2 \cdot V2/C) \cdot fc \cdot \cos\theta \quad (5)$$

where the character V2 denotes the velocity of the organs 19 and the character $\theta$ denotes the angle between the direction of the travel of the ultrasonic wave and the direction of the motion of the organs 19.

The second Doppler signals Vdx2 and Vdy2 are expressed by the following equations (6) and (7) as in the case of the first Doppler signals Vdx1 and Vdy1.

$$Vdx2 = A2 \cdot \cos(2\pi \cdot fd2 \cdot t) \quad (6)$$

$$Vdy2 = A2 \cdot \sin(2\pi \cdot fd2 \cdot t) \quad (7)$$

where the character A2 denotes a constant representing the amplitude.

As is understood from the comparison between the equations (3), (4), (6), and (7), the accurate signal component fd1 can be derived by determining the phase difference between the first Doppler signals Vdx1 and Vdy1 and the second Doppler signals Vdx2 and Vdy2. This process is executed by the phase difference calculator 11.

The phase difference calculator 11 determines a phase difference between the first Doppler signals Vdx1 and Vdy1 and the second Doppler signals Vdx2 and Vdy2 outputted from the sample-and-hold circuits 10a–10d. The phase difference calculator 11 derives a pair of orthogonal final Doppler signals Vdx and Vdy from the first and second Doppler signals through the phase difference calculation.

Figure 3:
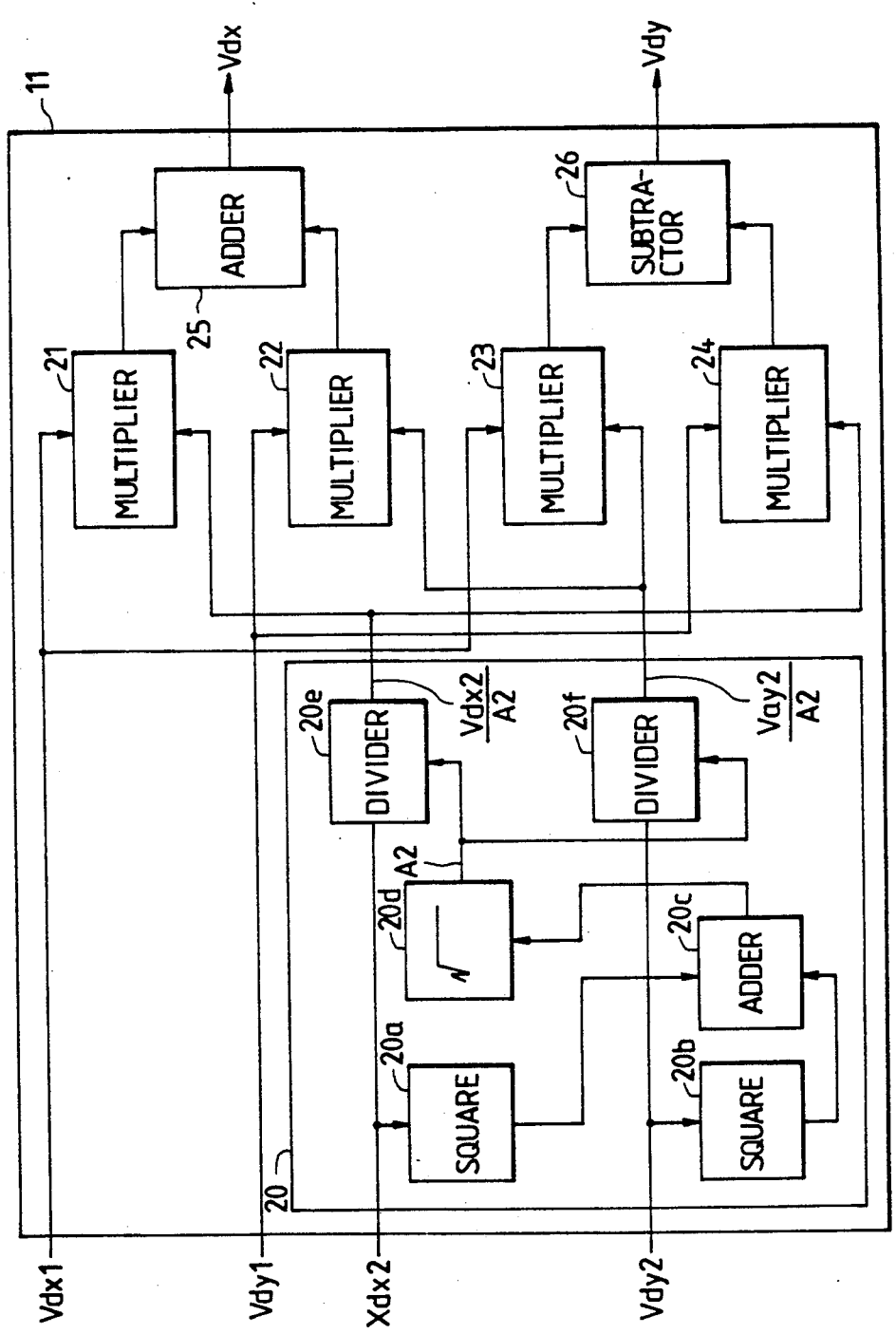
FIG. 3 is a block diagram of the phase difference calculator of FIG. 1.

As shown in FIG. 3, the phase difference calculator 11 includes an AGC circuit 20 in which squaring devices 20a and 20b square the second Doppler signals Vdx2 and Vdy2 respectively. The output signals from the squaring devices 20a and 20b are added by an adder 20c. A square root device 20d derives the amplitude A2 by calculating the square root of the output signal from the adder 20c. Dividers 20e and 20f divides the second Doppler signals Vdx2 and Vdy2 by the amplitude A2 calculated by the square root device 20d. The output signals Vdx2/A2 and Vdy2/A2 are expressed by the following equations (8) and (9).

$$Vdx2/A2 = \cos(2\pi \cdot fd2 \cdot t) \quad (8)$$

$$Vdy2/A2 = \sin(2\pi \cdot fd2 \cdot t) \quad (9)$$

The phase difference calculator 11 also includes multipliers 21, 22, 23, and 24. The multiplier 21 calculates the product of the first Doppler signal Vdx1 and the output signal Vdx2/A2 from the divider 20e. The multiplier 22 calculates the product of the first Doppler signal Vdy1 and the output signal Vdy2/A2 from the divider 20f. The multiplier 23 calculates the product of the first Doppler signal Vdx1 and the output signal Vdy2/A2 from the divider 20f. The multiplier 24 calculates the product of the first Doppler signal Vdy1 and the output signal Vdx2/A2 from the divider 20e. An adder 25 derives the final Doppler signal Vdx by adding the output signals from the multipliers 21 and 22. A subtracter 26 derives the final Doppler signal Vdy by subtracting the output signal of the multiplier 24 from the output signal from the multiplier 23. The final Doppler signals Vdx and Vdy are expressed by the following equations (10) and (11).

$$Vdx = A1 \cdot \cos(2\pi \cdot fd1 \cdot t) \quad (10)$$

$$Vdy = A1 \cdot \sin(2\pi \cdot fd1 \cdot t) \quad (11)$$

As understood from the equations (10) and (11), the final Doppler signals Vdx and Vdy are substantially free from the clutter components represented by the factor fd2.

The final Doppler signals Vdx and Vdy are fed from the phase difference calculator 11 to the analog-to-digital converters 13a and 13b via the high pass filters 12a and 12b respectively. The high pass filters 12a and 12b further remove clutter components from the Doppler signals Vdx and Vdy. The devices 13a and 13b convert the Doppler signals Vdx and Vdy into corresponding digital Doppler signals applied to the frequency analyzer 14. The device 14 analyzes the frequency of the digital Doppler signals. The display 15 indicates a result of the frequency analyzation of the digital Doppler signals which is performed by the frequency analyzer 14.

DESCRIPTION OF THE SECOND PREFERRED EMBODIMENT

Figure 4:
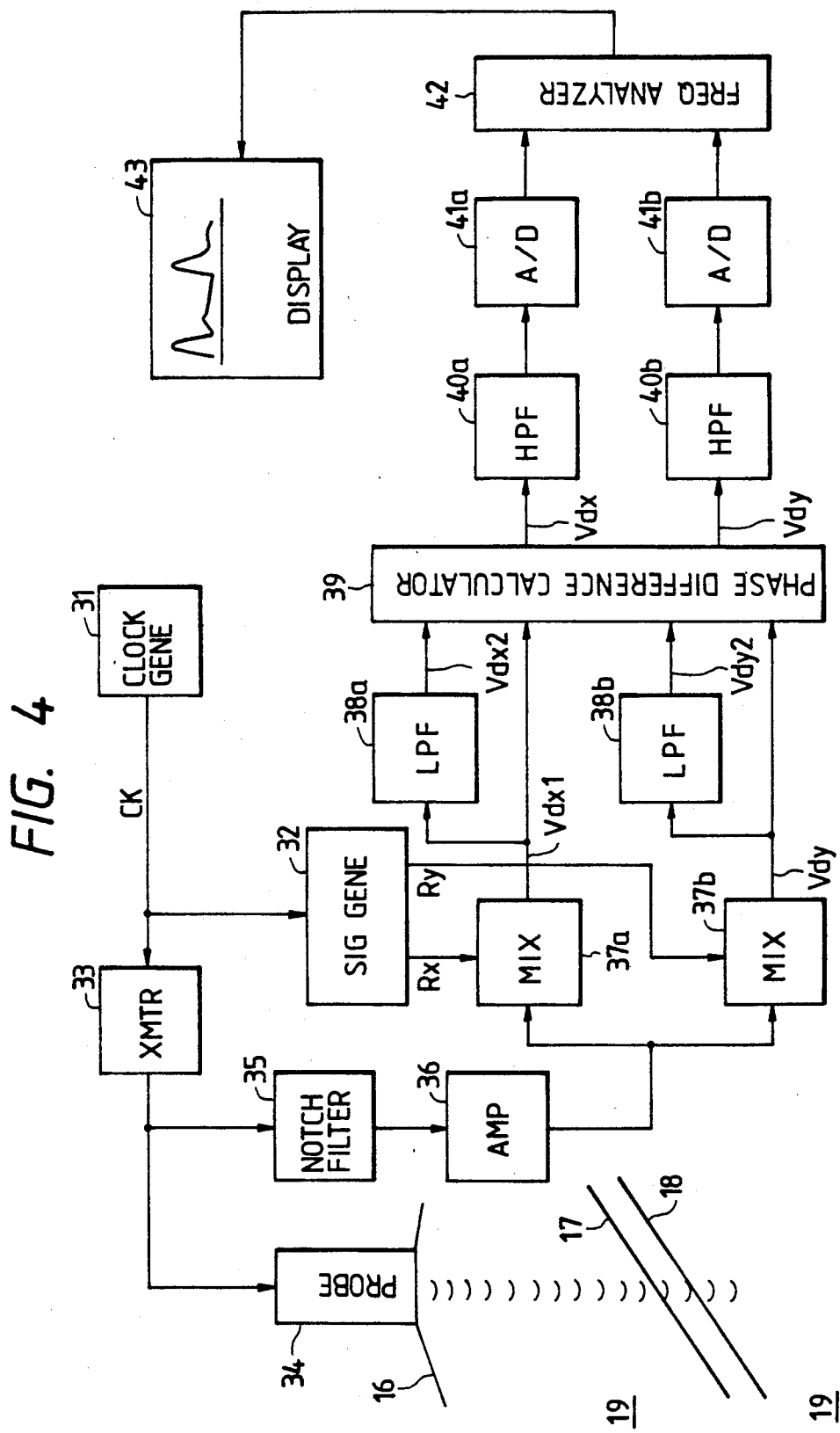
FIG. 4 is a block diagram of an ultrasonic blood velocity detector according to a second embodiment of this invention.

With reference to FIG. 4, a CW-type (continuous wave type) ultrasonic blood velocity detector includes a clock generator 31 which outputs a clock signal CK to an orthogonal signal generator 32 and a transmitter 33.

The orthogonal signal generator 32 derives a pair of orthogonal reference signals Rx and Ry from the clock signal CK through a frequency division process and a phase shift process. The reference signals Rx and Ry are orthogonal to each other and have a phase difference of 90°.

The transmitter 33 generates a continuous drive signal in response to the clock signal CK. The drive signal is outputted from the transmitter 33 to an ultrasonic probe 34. The ultrasonic probe 34 converts the drive signal into a continuous beam of corresponding ultrasonic wave and emits the ultrasonic beam into an examined body 16. Echoes of the ultrasonic beam are generated within the body 16 and portions of the echoes return to the ultrasonic probe 34. The ultrasonic probe 34 converts the ultrasonic echoes into a corresponding echo signal or received signal.

The echo signal is fed from the ultrasonic probe 34 to mixers 37a and 37b via a notch filter 35 and an amplifier 36. The notch filter 35 removes frequency-unshifted components from the echo signal. The mixer 37a processes the echo signal into a first detection signal Vdx1 through orthogonal detection or phase detection by use of the reference signal Rx outputted from the orthogonal signal generator 32. Similarly, the mixer 37b processes the echo signal into a second detection signal Vdy1 through orthogonal detection or phase detection by use of the reference signal Ry outputted from the orthogonal signal generator 32.

A low pass filter 38a derives a first clutter signal Vdx2 by extracting low-frequency clutter components from the first detection signal Vdx1 outputted from the mixer 37a. A second low pass filter 38a derives a second clutter signal Vdy2 by extracting low-frequency clutter components from the second detection signal Vdy1 outputted from the mixer 37b.

A phase difference calculator 39 determines a phase difference between the detection signals Vdx1 and Vdy1 and the clutter signals Vdx2 and Vdy2 outputted from the devices 37a, 37b, 38a, and 38b. The phase difference calculator 11 derives a pair of orthogonal Doppler signals Vdx and Vdy from the detection signals Vdx1 and Vdy1 and the clutter signals Vdx2 and Vdy2 as in the embodiment of FIGS. 1-3.

The Doppler signals Vdx and Vdy are fed from the phase difference calculator 39 to analog-to-digital converters 41a and 41b via high pass filters 40a and 40b respectively. The high pass filters 40a and 40b remove clutter components from the Doppler signals Vdx and Vdy. The devices 41a and 41b convert the Doppler signals Vdx and Vdy into corresponding digital Doppler signals applied to a frequency analyzer 42. The device 42 analyzes the frequency of the digital Doppler signals. A display 43 indicates a result of the frequency analyzation of the digital Doppler signals which is performed by the frequency analyzer 42.

The ultrasonic blood velocity detector operates as follows. The clock generator 1 outputs the clock signal CK which has a constant frequency. The orthogonal signal generator 2 derives a pair of the orthogonal reference signals Rx and Ry from the clock signal CK through a frequency division process and a phase shift process. The reference signals Rx and Ry have a predetermined frequency fc and are 90° out of phase from each other.

The transmitter 33 derives the continuous drive signal by frequency-dividing the clock signal CK. The drive signal also has the predetermined frequency fc. The drive signal is outputted to the ultrasonic probe 34 in contact with the examined body 16. The ultrasonic probe 34 converts the drive signal into a continuous beam of corresponding ultrasonic wave and emits the ultrasonic beam into the examined body 16. Echoes of the ultrasonic beam are generated at internal portions of the examined body 16 such as organs 19, a blood vessel 17, and blood 18 within the blood vessel 17. Parts of the echoes return to the ultrasonic probe 34. The ultrasonic probe 34 converts the ultrasonic echoes into the corresponding echo signal or received signal.

The notch filter 35 removes frequency-unshifted components or strong clutter components from the echo signal. The mixer 37a mixes the echo signal and the reference signal Rx and specifically processes the echo signal into the first detection signal (Doppler signal) Vdx1 through orthogonal detection or phase detection by use of the reference signal Rx. Similarly, the mixer 37b mixes the echo signal and the reference signal Ry and specifically processes the echo signal into the second detection signal (Doppler signal) Vdy1 through orthogonal detection or phase detection by use of the reference signal Ry. The detection signals Vdx1 and Vdy1 are expressed by the previously-mentioned equations (3) and (4).

The clutter signals Vdx2 and Vdy2 are extracted from the detection signals Vdx1 and Vdy1 by the low pass filters 38a and 38b. The clutter signals Vdx2 and Vdy2 are expressed by the previously-mentioned equations (6) and (7).

The phase difference calculator 39 derives the Doppler signals Vdx and Vdy from the detection signals Vdx1 and Vdy1 and the clutter signals Vdx2 and Vdy2 as in the embodiment of FIGS. 1-3. The Doppler signals Vdx and Vdy are expressed by the previously-mentioned equations (10) and (11).

The Doppler signals Vdx and Vdy are fed from the phase difference calculator 39 to the analog-to-digital converters 41a and 41b via the high pass filters 40a and 40b respectively. The high pass filters 40a and 40b further remove clutter components from the Doppler signals Vdx and Vdy. The devices 41a and 41b convert the Doppler signals Vdx and Vdy into corresponding digital Doppler signals applied to the frequency analyzer 42. The device 42 analyzes the frequency of the digital Doppler signals. The display 43 indicates a result of the frequency analyzation of the digital Doppler signals which is performed by the frequency analyzer 42.

What is claimed is:

1. An ultrasonic blood velocity detector comprising:
   an ultrasonic probe emitting ultrasonic waves into an examined body and converting echoes of the emitted ultrasonic waves into an echo signal;
   means for processing the echo signal into a detection signal through phase detection;
   means for deriving a first Doppler signal and a second Doppler signal from the detection signal, the first Doppler signal representing a flow of blood, the second Doppler signal mainly containing clutter components; and
   means for calculating a difference in phase between the first and second Doppler signals to detect blood velocity.

2. An ultrasonic blood velocity detector comprising:
   an ultrasonic probe emitting ultrasonic waves into an examined body and converting echoes of the emitted ultrasonic waves into an echo signal;
   means for generating trigger pulses at a predetermined period;
   means for generating a drive pulse signal synchronous with the trigger pulses;
   means for driving the ultrasonic probe by use of the drive pulse signal;
   means for generating a pair of reference signals orthogonal to each other;

means for processing the echo signal into a pair of detection signals through orthogonal detection by use of the pair of the reference signals;

means for integrating the pair of the detection signals for a first interval during which the echo signal represents a flow of blood within the examined body, and for converting the pair of the detection signals into a pair of first Doppler signals representing the flow of the blood, the first interval starting at a moment which follows each of the trigger pulses by a first predetermined time;

means for integrating the pair of the detection signals for a second interval during which the echo signal represents a motion of an organ within the examined body, and for converting the pair of the detection signals into a pair of second Doppler signals representing the motion of the organ, the second interval starting at a moment which follows each of the trigger pulses by a second predetermined time; and means for calculating a difference in phase between the pair of the first Doppler signals and the pair of the second Doppler signals to detect blood velocity.

3. An ultrasonic blood velocity detector comprising:

an ultrasonic probe emitting ultrasonic waves into an examined body and converting echoes of the emitted ultrasonic waves into an echo signal;

means for generating a continuous drive signal having a predetermined frequency;

means for driving the ultrasonic probe by use of the continuous drive signal;

means for generating a pair of reference signals orthogonal to each other and equal to the continuous drive signal in frequency;

means for processing the echo signal into a pair of Doppler signals through orthogonal detection by use of the pair of the reference signals;

a pair of low pass filters extracting clutter components from the Doppler signals and deriving a pair of clutter signals from the extracted clutter components; and means for calculating a difference in phase between the pair of the Doppler signals and the pair of the clutter signals to detect blood velocity.

* * * * *